(12) United States Patent
Cullum et al.

(10) Patent No.: US 7,504,202 B2
(45) Date of Patent: Mar. 17, 2009

(54) RAPID IMMUNOASSAY OF ANTHRAX PROTECTIVE ANTIGEN IN VACCINE CULTURES AND BODILY FLUIDS BY FLUORESCENCE POLARIZATION

(75) Inventors: Malford E. Cullum, Grayslake, IL (US); Paul Hine, Holt, MI (US); Lloyd G. Simonson, Spring Grove, IL (US); Chun N. Shih, East Lansing, MI (US); Diane R. Bienek, Lindenhurst, IL (US); Sukjoon Park, Germantown, MD (US); James C. Ragain, Jr., Great Lakes, IL (US); Linda A. Lininger, Grayslake, IL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 582 days.

(21) Appl. No.: 10/809,877

(22) Filed: Mar. 26, 2004

(65) Prior Publication Data

US 2004/0235075 A1    Nov. 25, 2004

Related U.S. Application Data

(60) Provisional application No. 60/457,940, filed on Mar. 28, 2003.

(51) Int. Cl.
*C12Q 1/00*    (2006.01)

(52) U.S. Cl. ............................ 435/4; 435/7.93; 435/34; 436/518; 530/350

(58) Field of Classification Search ................. 435/4, 435/34, 7.93; 436/518; 530/350
See application file for complete search history.

(56) References Cited

U.S. PATENT DOCUMENTS 6,927,068 B2 *   8/2005   Simonson et al. ............ 436/518
6,955,891 B2 *  10/2005   Cunningham et al. ......... 435/34

OTHER PUBLICATIONS

Tencza et al (J. Clin.Microbiol. May 2000. 38(5): 1854-1859).*
Nielsen et al (J.Immunolg. Methods. 1996. 195: 161-168).*

* cited by examiner

*Primary Examiner*—Jennifer E Graser
(74) *Attorney, Agent, or Firm*—Ning Yang; Joseph K. Honby, Jr.

(57) ABSTRACT

The inventive subject matter relates to a competitive method for estimating the concentration in a sample of a *Bacillus anthracis* protein or antibody thereof selected from the group consisting of protective antigen (PA), lethal factor (LF) and edema factor (EF). The method may employ the use of Fluorescence Polarization, FLT or FRET. The competitive methods are capable of detecting a target protein within 5 minutes within the range of 0.1 to 10.0 nM. The methods provide for the rapid detection and quantitation of bacteria, bacterial antigen or antibody in culture media or broth of growing cultures of bacteria, including *B. anthracis* by fluorescent methods.

11 Claims, 1 Drawing Sheet

RAPID IMMUNOASSAY OF ANTHRAX PROTECTIVE ANTIGEN IN VACCINE CULTURES AND BODILY FLUIDS BY FLUORESCENCE POLARIZATION

CROSS REFERENCE TO RELATED APPLICATION

This application claims priority to U.S. Provisional application 60/457,940 filed Mar. 28, 2003.

FIELD OF THE INVENTION

The inventive subject matter relates to a competitive fluorescence method for estimating the concentration in a sample of *Bacillus anthracis* protein or specific antibody. The method contemplates the use of FLT, FRET or FP.

BACKGROUND OF INVENTION

Oral fluids have been increasingly recognized as acceptable alternatives to serum for use in diagnostic tests for certain hormones, drugs, antibodies and antigens. However, diagnostic assays utilizing saliva and other oral fluids appear as entries in the National Library of Medicine MEDLARS database with a frequency of only 1 in 30 and 1 in 100, respectively, when compared to entries in which blood serum is reported. Oral fluids are collected without pain, needle sticks, or religious and social prohibitions, and use of these involves minimal risk or exempt protocols for the use of human subjects. The Department of Defense (DoD) has made salivary diagnostics a Future Naval Capability (FNC), and both the Office of Naval Research (ONR) and the Military Infectious Disease Research Program (MIDRP) of the US Army have funded projects to investigate the use of oral fluids or saliva to diagnose disease or monitor immunization status. The military has had a long-standing interest in saliva with ONR compiling in 1960 a review of all saliva references in the literature from 1888-1957 (1). In 1965, the US Army Medical Research Development Command supported a contract that published one of the first reports of human salivary antibodies to indigenous bacteria (2). The United States Department of Agriculture (USDA) recently sponsored a symposium to advance non- or minimally-invasive technologies to monitor health and nutritional status in the Special Supplemental Nutrition Program for Women, Infants and Children (WIC) using saliva as a diagnostic tool (3, 4). These considerations and continuing improvements in standardization of collection methods make these body fluids the diagnostic media of choice in the 21$^{st}$ century.

Recent reviews of the clinical chemistry and microbiology of saliva (5), the roles of saliva in health and disease (6), in diagnosing periodontal disease (7), and as a diagnostic fluid (8) indicate the growing prominence this matrix plays in medical diagnostics (9, 10). Saliva (6) and oral fluid (11) are distinct biochemically. They generally reflect the serum pool, but neither is a passive ultrafiltrate (passive requires no direct ATP use) of serum as previously thought (12). The presence of mucins, the polyanionic glycoproteins that increase salivary viscosity, and oral flora have been largely responsible for the lack of popularity of oral fluids in clinical research. Saliva presents several challenges for diagnostics: limited reference values have been published and the standardization of sample collection has fallen behind serum (13). Standardized saliva (14) and oral fluid (15) collection devices have only recently become available and should contribute to further investigations. Antibody containing oral fluids, gingival crevicular fluid (GCF) and oral mucosal transudate (OMT) arise due to hydrostatic pressure of the capillaries and venules associated with the lingual or buccal epithelium. They offer less variation than saliva and the best alternative to serum for antibody detection (16). GCF is similar to serum in protein composition but is significantly lower in protein concentration, being about 3% of the protein levels in blood (17,18). GCF volume is about one percent of total saliva volume in the healthy mouth (19). GCF is obtained by inserting an absorbent paper into the pocket or sulcus of a tooth (between the tooth and gingiva) after clearing the supragingival plaque (20). Its medical and dental use has not been reviewed since the 1970's (21, 22). OMT is 3-4 fold higher in protein concentration than saliva based on the IgG obtained using this device and is collected by placing a thick pad against the buccal mucosal surface juxtaposed between the parotid duct and the gingival crest (11). A current OMT device uses a salt-impregnated pad that is subsequently treated to release the antibody-containing fluid and retain the glycoproteins on the pad yielding "oral fluid". One such oral fluid collection device has been licensed by Abbott Laboratories and eliminates the necessity for venipuncture (23).

The oral cavity as an immunological entity has been reviewed with respect to oral diseases (24) and microbiology (19). The use of oral fluids in diagnostic immunology includes detection of HIV (25); measles, mumps and rubella (26); hepatitis A (27); B (28); and C (29); *Helicobacter pylori* (30); dengue (31); and Chagas' disease (32). The current review will focus on the use of fluorescence polarization (FP)-based tests to detect antibodies to anthrax vaccine and to tuberculosis exposure using saliva, GCF or OMT as a test fluid.

Currently excepted methods for the clinical evaluation of patients using serum and oral fluids include enzyme-linked immunosorbent assays (ELISA), agglutination or radioimmunoassays (RIA). However, FP has distinct advantages over previous methods. Because FP is conducted in a fluid environment and because polarization is a general property of fluorescent molecules, FP assays have the potential to be less susceptible to non-specific interactions occurring at the cell surface and to interferences present in non-homogeneous sample fluids. However, despite the clear advantages of FP in diagnostics, only a limited number of non-commercial laboratories have adopted FP for detection of antibody in serum samples (33-35). High throughput screening (HTS) laboratories, on the other hand prefer FP based assays as a component of an automatable system capable of real-time evaluation of samples that are robust, flexible, sensitive and consistent with historical data (36).

Fluid-based assays are highly adaptable to the direct evaluation of oral fluids, saliva and serum for exposure to infectious agents including HIV, measles, mumps, rubella, hepatitis, *Helicobacter pylori*, dengue disease (37-43). Salivary and oral fluid assays have been increasingly recognized as a better, non-invasive alternative to serum-based diagnostics in detecting certain hormone, drug, antibody and antigen detection (44, 45).

Infectious disease rates and immunization strategies are critical to public health as well as a component of military preparedness. An integral component of the U.S. immunization strategy is the production of effective vaccines against agents such as *Bacillus anthracis* (anthrax) as well as other emerging organisms such *Mycobacterium tuberculosis* and *M. bovis*, the causative agents of *tuberculosis* (47).

Pathology due to *B. anthracis* infection is primarily due to the release by the organism of "protective antigen" (PA) in association with lethal factor (LF) and edema factor (EF)

(48). The complete DNA and protein sequence of PA has been published and its three-dimensional structure is known from x-ray crystallography (49). The characteristics and biological functions of the four domains of PA are also available permitting selection of epitopes within the domains based on antigenic properties (49-53). In animal studies, as well as studies of natural human infection, it was shown that individuals who survived an infection produced antibodies to PA suggesting its importance in protection (54).

Vaccination for anthrax occurs for all Department of Defense personnel deploying to at-risk areas of operation. Furthermore, research personnel working with infectious strains of anthrax are vaccination, prophylactically. The current human anthrax vaccine (adsorbed) (AVA) licensed in the United States contains aluminum hydroxide adjuvant and consists mostly of PA from an attenuated, non-encapsulated strain of B. anthracis (55,56). Several recombinant PA experimental plasmids have been produced which could be important as a vaccine component against the disease.

The production of bacteria or their products for use in vaccines requires routine monitoring of bacterial growth to obtain the material in optimum quantities and in a form most suitable for eliciting immunity. Expression of specific proteins, depending on the organism, is to a great extent dependent on the phase of bacterial cell growth in culture and the density of the protein or organism. Routine monitoring of growing cultures is, therefore, important. Assays for bacterial growth monitoring, must be relatively accurate, sensitive and able to be conducted in near real-time. Furthermore, the assay must be able to operate in the face of turbid media containing interfering substances, not related to the target protein being measured.

Current methods available to monitor bacterial growth include optical density measurement, which gives an estimation of bacterial density but no direct measure of specific protein concentrations being produced. More accurate methods include Western blot; enzyme-linked immunosorbent assay (ELISA); dot blots; which is a form of ELISA and polyacrylamide gel electrophoresis in sodium dodecyl sulfate (SDS-PAGE). ELISA methods, however, are inadequate due to either low sensitivity or erroneous results caused by interference effects by media constituents. SDS-PAGE methods are inadequate because they do not give real time information such that a culture composition cannot be estimated with accuracy given the time span between culture SDS-PAGE and interpreting the SDS-PAGE results.

Fluorescent polarization (FP) technology is capable of rapid, real-time, sensitive evaluation of fluid phase antigens with high specificity (57, 58). FP based assays are predicated on the principle that polarized incident visible or ultraviolet light that illuminates a fluorochrome causes subsequent polarized fluorescence with emission at a longer wavelength. However, molecules in solution are capable of rotation. Therefore, polarized light striking a fluorescent molecule loses polarization due to rotation of the molecule. Solutions containing slower turning, large molecule-fluorochrome complexes tends to stay polarized longer verses situations where smaller labeled molecules are present. In order to accommodate molecules of different sizes (up to $10^7$ kDa molecular weight), different fluorochromes can be selected (59).

Combining fluorochrome-labeled antigen or peptide with antibody results in an increase in FP, as measured in arbitrary millipolarization (mP) units. The smaller the fluorescent antigen, the greater the increase in mP units that is measured upon binding to its counterpart antibody, since mP depends upon the partial specific volume (approximate molecular weight in solution) of the labeled substance. The dependence is non-linear but is describable in a Perrin equation (66).

FP antigen-antibody binding assays require only the mixing of fluorescent reagent (antigen) with the sample (containing antibody) in a liquid buffer. In a rapid diagnostic format, essentially two FP readings are necessary; a base-line reading and a reading after a specified time. The FP value increases as binding of antigen and antibody occurs in a direct binding assay. The difference in FP between a fluorescent antigen of 10 kDa initially and the fluorescent complex consisting of it and IgG, for example, results in a measurable association using less than saturating antibody concentrations (60).

A distinct advantage of FP technology is that assays can accommodate somewhat cloudy solutions, such as bacterial suspensions or variations in total fluorescence that are present in non-homogenous solutions, such as bacterial broth, urine or oral fluids. Furthermore, FP assays can be designed to accommodate significant variation in pH in fluid samples, such as in some media or in saliva or urine, by utilizing different pH-independent fluorochromes (61).

Currently, FP assays are in used to measure different types of binding reactions, to follow proteolytic reactions and to measure various enzymatic or receptor binding reactions (62, 63). In clinical settings, FP assays are used to measure the level of drugs, hormones or antibiotics in blood plasma (64). ELISA, RIA and immunoprecipitation assays are the most accepted methods for detection of antibody in serum samples (60, 65, 66). However, FP, because of its advantages over other detection methods is well-suited as a diagnostic tool for analyzing formerly difficult to evaluate samples such as oral fluids and saliva, in addition to serum, for the quantitative assessment of specific antibody, diagnostic markers, drugs, chemicals and infectious or biohazardous agents.

A further aspect of the invention is the detection and quantitation of protective antigen, lethal factor and edema factor from Bacillus anthracis in saliva, blood, oral fluids or other bodily fluids and tissues. Current vaccines to B. anthracis are directed against PA. Furthermore, because of the importance of lethal factor and edema factor in the pathology of anthrax, detection of these genes in body fluids or broth cultures is also important. Therefore, an inventive aspect is the specific, sensitive and rapid detection of PA in bodily fluids including saliva, and oral fluids and environmental samples.

SUMMARY OF THE INVENTION

Current methods for the monitoring of growing broth cultures of bacteria for vaccine production, including ELISA and SDS-PAGE, are inadequate. ELISA exhibits high levels of interference by media constituents leading to low fidelity of results and concomitant low sensitivity of detection. SDS-PAGE, like ELISA is extremely time consuming making the method unsuitable for routine monitoring. Therefore, a method that is sensitive, rapid and that gives predictable results is important in order to optimize production of bacterial vaccine components, including the vaccine components for B. anthracis, protective antigen (PA).

An object of the invention is an assay for the rapid detection and quantitation of bacteria in culture media or broth of growing cultures of B. anthracis by competitive fluorescent polarization (FP), fluorescence lifttime (FLT) analysis or fluorescence resonance energy transfer (FRET). Another object of the invention is a rapid, real-time detection method for monitoring growing bacterial cultures or bodily fluids. A still further object is an assay capable of sensitive, rapid detection of bacterial media or bodily fluids without interference from sample constituents. A still further object is the real-time quantitation of protective antigen (PA) in growing cultures of *B. anthracis*. A still further object is the quantitation of lethal factor (LF) in growing cultures of *B. anthracis*. still further object is the quantitation of edema factor (EF) in growing cultures of *B. anthracis*. A still further object is the detection of PA, LF and EF in bodily fluids, including saliva and oral fluids and in environmental samples.

These and other objects of the invention are accomplished by an assay employing fluorescent polarization in a competitive assay procedure.

DETAILED DESCRIPTION

Figure 1:
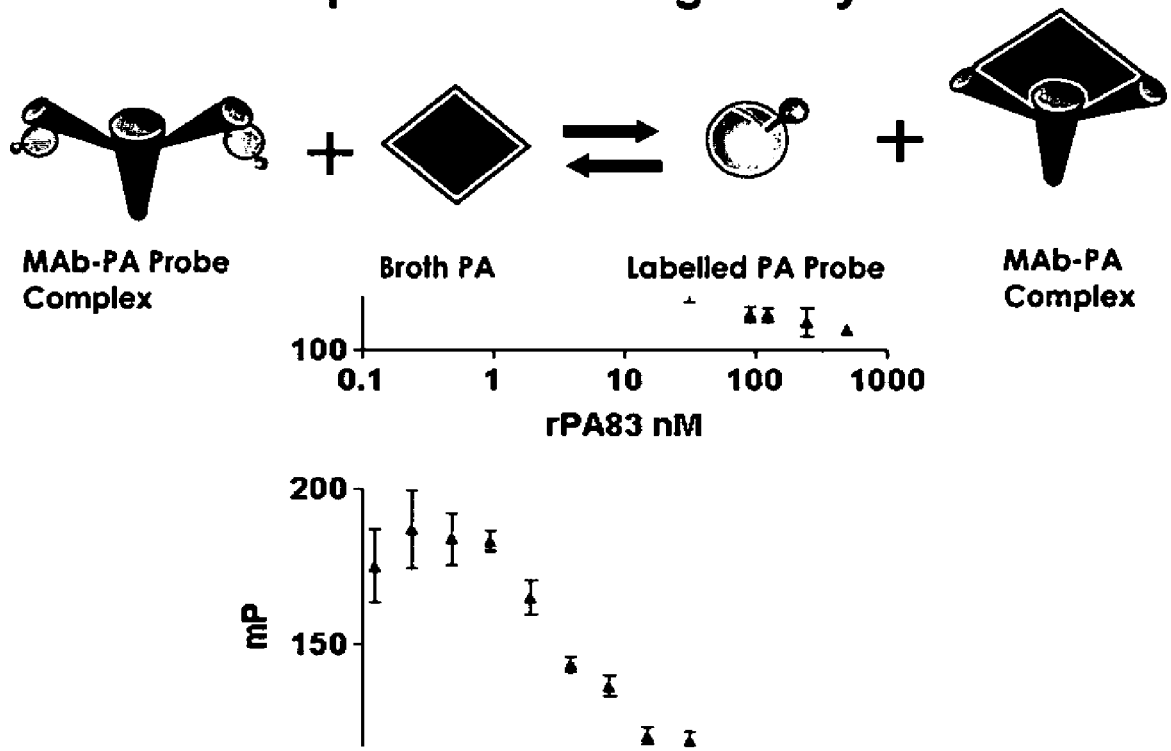
FIG. 1. Diagram showing expected change in polarization at various concentrations of competitive protein. For complete description, see example 1.

Fluorescent polarization holds great promise as an assay method for frequent, routine, cost-effective means of obtaining quantitation of bacterial proteins in growing bacterial broth cultures. Fluorescent molecules emit polarized fluorescence when they absorb polarized light at a specific wavelength. However, inherent in molecules in solution is their tendency to rotate. When polarized light strikes the molecules in solution, the emitted light does not remain polarized because the molecule is rotating rapidly in solution. The rate of rotation, however, is dependent on the size of the molecule. Therefore, an antigen/antibody complex will have an inherently slower rate of rotation causing more of the polarized fluorescence to be emitted in the same plane as the incident light. The polarization-based readouts are less susceptible to environmental interferences, such as pH, cloudiness, and particles in the assay compartment than other light-based assays. FP is fundamentally and theoretically different from most color based photometric techniques and gains its analytical advantage by this intrinsic property of being independent of concentration. The current application utilizes FP technology in a competitive assay to quantitate bacterial protein concentration in growing bacterial broth cultures. The invention is designed to be capable of determining the concentration of antigen in fermentation broth.

An aspect of the invention is a competitive method for estimating the concentration of *Bacillus anthracis* proteins such as protective antigen (PA), lethal factor (LF) and edema factor (EF). The assay method incorporates the broad detection technologies of fluorescence polarization (FP), fluorescence life-time (FLT) and fluorescence resonance energy transfer (FRET). The general scheme of the assay includes the following steps:
 a. intermixing a sample, suspected of containing a *B. anthracis* PA, LF or EF with a specific antibody and a competitive reagent, suitable as a ligand for the specific antibody and labeled a fluorochrome;
 b. incubating the competitive reagent and specific antibody for 15 seconds to 5 minutes, depending on suspected concentration of the target antigen in the sample;
 c. detecting the binding interaction of PA, LF or EF and specific antibody.

Detection of specific agent would then be by either a change in fluorescence polarization or a change in fluorescence life-time, depending on whether the technology incorporated FP or FLT, respectively. If the method incorporated FRET, then detection is by sensitized fluorescence of the acceptor or by quenching of donor fluorescence or by fluorescence depolarization. Furthermore, the competitive reagent used in the assay can be either native or recombinant PA, LF or EF or fragments thereof.

Furthermore, an aspect of the invention is that different fluorochromes can be utilized in order to optimize results, including the incorporation of pH-independent fluorochromes. The fluorochromes that are included as an aspect of the invention include: 7-AAD, Acridine Orange, Alexa 488, Alexa 532, Alexa 546, Alexa 568, Alexa 594, Aminonapthalene, Benzoxadiazole, BODIPY 493/504, BODIPY 505/515, BODIPY 576/589, BODIPY FL, BODIPY TMR, BODIPY TR, Carboxytetramethylrhodamine, Cascade Blue, a Coumarin, Cy2, CY3, CY5, CY9, Dansyl Chloride, DAPI, Eosin, Erythrosin, Ethidium Homodimer II, Ethidium Bromide, Fluorescamine, Fluorescein, FTC, GFP (yellow shifted mutants T203Y, T203F, S65G/S72A); Hoechst 33242, Hoechst 33258, IAEDANS, an Indopyras Dye, a Lanthanide Chelate, a Lanthanide Cryptate, Lissamine Rhodamine, Lucifer Yellow, Maleimide, MANT, MQAE, NBD, Oregon Green 488, Oregon Green 514, Oregon Green 500, Phycoerythrin, a Porphyrin, Propidium Iodide, Pyrene, Pyrene Butyrate, Pyrene Maleimide, Pyridyloxazole, Rhodamine 123, Rhodamine 6G, Rhodamine Green, SPQ, Texas Red, TMRM, TOTO-1, TRITC, YOYO-1, vitamin B12, flavin-adenine dinucleotide, and nicotinamide-adenine dinucleotide.

The assay method is generally adaptable to the detection of PA, LF or EF in bacterial culture media as well as in other bodily fluids including: saliva, oral rinse expectorant, oral fluid including oral mucosal transudate and gingival crevicular fluid, urine, sweat, tears, blood, serum, stool, gastric fluid, synovial fluid, phlegm, and other clinical and laboratory specimens and samples. The time of assay will depend on expected concentration in the sample. For bacterial cultures that has progressed near or past the logarithmic phase of its growth curve, it is estimated that 30 minutes or less will be required for incubation with specific antibody.

The results of test samples will be compared to results obtained from negative or positive control results, using either FP, FLT or FRET technology. Negative controls will contain the same fluorochrome-labeled competitive reagent as used in the test sample. A positive control can also contain the same fluorochrome-labeled competitive reagent as in the test sample but will be exposed to a known amount of said protein. The measured results of the test samples will then be compared to either or both of the negative or positive controls. It is estimated that the sensitivity of detection of *B. anthracis* protein will occur down to at least 5 μg/ml (6 nM) or less. The required time for the assay will be less than 5 minutes (see Prophetic Example 1).

In addition to detection *B. anthracis* proteins in various samples types, a still further aspect of the invention is the detection of specific antibody to PA, LF or EF in bodily fluids by an assay method incorporation FP, FLT or FRET technology. The bodily fluids that are included as an aspect of the invention include: saliva, oral rinse expectorant, oral fluid including oral mucosal transudate and gingival crevicular fluid, urine, sweat, tears, blood, serum, stool, gastric fluid, synovial fluid, phlegm, and other clinical and laboratory specimens and samples.

The inventive subject matter for the detection of specific antibodies to *B. anthracis* proteins includes the steps:
 a. intermixing a sample, suspected of containing specific antibody with a competitive reagent labeled with a fluorochrome, capable of binding to the specific antibody;
 b. incubating the sample, containing specific antibody, and competitive reagent for 15 seconds to 5 minutes;
 c. detecting binding interaction between said protein and antibody.

Detection of specific agent would then be by either a change in fluorescence polarization or a change in fluorescence life-time, depending on whether the technology incorporated was FP or FLT, respectively. If the method incorporated FRET, then detection is by sensitized fluorescence of the acceptor or by quenching of donor fluorescence or by fluorescence depolarization.

The results of test samples will be compared to results obtained from negative or positive control results, using either FP, FLT or FRET technology. Negative controls will contain the same fluorochrome-labeled competitive reagent as used in the test sample. A positive control can also contain the same fluorochrome-labeled competitive reagent as in the test sample but will be exposed to a known amount of said protein. The measured results of the test samples will then be compared to either or both of the negative or positive controls.

It is estimated, like for detection of antigen, the assay will take less than 5 minutes to complete. Less time will be required for samples with high antibody titers (30 seconds or less incubation time). Also, like for detection of antigen, an inventive aspect is the ability to select fluorochromes, depending on sample conditions, including pH-independent fluorochromes. The fluorochromes available, as an aspect of the invention, include: 7-AAD, Acridine Orange, Alexa 488, Alexa 532, Alexa 546, Alexa 568, Alexa 594, Aminonapthalene, Benzoxadiazole, BODIPY 493/504, BODIPY 505/515, BODIPY 576/589, BODIPY FL, BODIPY TMR, BODIPY TR, Carboxytetramethylrhodamine, Cascade Blue, a Coumarin, Cy2, CY3, CY5, CY9, Dansyl Chloride, DAPI, Eosin, Erythrosin, Ethidium Homodimer II, Ethidium Bromide, Fluorescamine, Fluorescein, FTC, GFP (yellow shifted mutants T203Y, T203F, S65G/S72A), Hoechst 33242, Hoechst 33258, IAEDANS, an Indopyras Dye, a Lanthanide Chelate, a Lanthanide Cryptate, Lissamine Rhodamine, Lucifer Yellow, Maleimide, MANT, MQAE, NBD, Oregon Green 488, Oregon Green 514, Oregon Green 500, Phycoerythrin, a Porphyrin, Propidium Iodide, Pyrene, Pyrene Butyrate, Pyrene Maleimide, Pyridyloxazole, Rhodamine 123, Rhodamine 6G, Rhodamine Green, SPQ, Texas Red, TMRM, TOTO-1, TRITC, YOYO-1, vitamin B12, flavin-adenine dinucleotide, and nicotinamide-adenine dinucleotide.

For both detection of *B. anthracis* antigen as well as antibody, specific for *B. anthracis* proteins, an aspect of the invention is that a fluorochrome concentration of 1 nM or less will yield a sample millipolarization increase or decrease of at least 10 mP. A further aspect is that the method will have a specificity of 96-99% for the detection of specific antibody or antigen in bodily fluids or culture.

PROPHETIC EXAMPLE 1

Competitive FP Assay for Measuring Broth Protective Antigen, Lethal Factor and Endema Factor of *Bacillus anthracis*

Quantitative, real-time monitoring of growing bacterial cultures is necessary to ensure maximum production of important bacterial proteins in vaccine production. *Bacillus anthracis* is of particular importance due to its potential public health and military focus as a potential bioterrorism weapon. Monitoring of growing cultures of *B. anthracis* is conducted by the following steps:
a) Add 10 µl of labeled competitor peptide (e.g. FITC labeled PA, lethal factor or edema factor) in 1 ml buffer;
b) Read blank;
c) Add 20 µl of monoclonal antibody to target protein in said 1 ml buffer;
d) Incubate for 2 minutes;
e) Read the FP of the tracer;
f) Add 10 µl of culture broth to said 1 ml buffer in step d);
g) Read decrease in mP. The decrease in mP is proportional to the PA concentration.

Culture broths of *B. anthracis* contain protective antigen concentrations up to 5 ug/ml. Therefore the assayable range of protective antigen required for FP assay is similar to that for ELISA assay. Using standard sandwich ELISA techniques, recombinant PA reports approximately 0.01 OD per 1 ng PA at 405 nm using horse radish peroxidase substrate conjugated antibodies in a range of 1.5-200 ng protective antigen. An example standard ELISA was used to estimate protective antigen in serial dilutions of buffer from 25 nM (2 ug/ml) down to 0.2 nM (16 ng/ml).

Similar results are expected in competitive fluorescence polarization as immunoassay techniques (see FIG. 1). Combining an fluorescent dye-labeled protective antigen probe at about 1 nM (labeled PA probe) and a monoclonal (MAb) or polyclonal (PAb) antibody at an adequate dilution (usually between 1:25-1:250K) would report numbers around 200 mP (left side of equation and left side of graph as shown in FIG. 1). Culture broth would be added as unlabeled competitor (broth PA) in a range of 0.01-0.1 ml depending on how long the culture had grown causing dissociation of the labeled probe from the antibody. Dissociation of the labeled probe from the antibody in the presence of increasing amounts of broth PA results in increasing amounts of free labeled probe and decreasing mP readings that are proportional to the concentration of protective antigen in the culture broth. (Right side of the equation and right side of the graph). At full growth, the assay mixture would require 0.01 ml broth (5 ug/ml protective antigen, about 6 nM) while partial growth would require proportionately more broth up to 0.1 ml to estimate a similar concentration. Other optional reagents may be used to suppress intrinsic culture broth fluorescence.

EXAMPLE 2

Determining the Concentration of Recombinant or Native Protective Antigen (PA) of *Bacillus anthracis* Antigen in Fermentation Broth Overlapping 15 and 25 mer peptide sequences were synthesized from the amino acid region 1-764 of full-length PA using Fmoc (9-fluorenylmethoxycarbonyl) chemistry including a final step to attach an N-terminal 6-carboxyfluorescein (FAM). Enzymatic digests of fluorescein-6-isothiocyanate (FITC isomer II) labeled full length PA were made with trypsin, pepsin and chymotrypsin. These peptides were screened for specific antibody binding by immune sera. Using Western Blot, ELISA and dot-blot analysis, a 10-mer portion of domain 4 of the COOH region of PA was suitable as an FP probe, a 5-6 kDa portion of domain 3 and domain 4 was suitable as an FP probe, a 10 kDa portion of domain 3 and 4 was suitable as a FP probe, a 5-6 kDa portion of domain 1 and 2 was suitable as a FP probe, and a 10 kDa portion of domain 1 and 2 was suitable as a FP probe Fermentation broth cultures of *Bacillus anthracis* (vaccine strain V770-NP1-R) containing PA were produced. Culture media is then mixed with antibody and competitive probe. Incubation times was less than 30 seconds for cultures nearing the stationary phase of growth and for less than 4 minutes for newly seeded cultures (and therefore low concentration of PA). At 1 nM probe concentration, the blank subtracted fluorescence polarization reading is determined to be quantifiable if mP decreased by at least 10 mP.

REFERENCES

1. Anonymous: Biography on Saliva; Library of Congress Bibliography Section Science & Technology Division; Office of Naval Research Report ACR-48, Washington, D.C., 1960. Library of Congress.
2. Kraus F, Konno J: The salivary secretion of antibody, Alabama J Med Sci 1965; 2:15-22.
3. Hirschman J D, Kresge J A: Synthesis of a symposium: innovative non- or minimally-invasive technologies for monitoring health and nutritional status in mothers and young children, J Nutr 2001; 131:1643S-5S.
4. Hofman L F: Human saliva as a diagnostic specimen, J Nutr 2001; 131:1621S-5S.
5. Tenovuo J: Human Saliva: Clinical Chemistry and Microbiology, 256. Vol. 1, Boca Raton, Fla., CRC Press, 1989.
6. Proceedings: Saliva in health and disease. Proceedings of the 16th International Conference on Oral Biology. Apr. 9-12, 2000. Chantilly, Va., USA. Proceedings, Adv Dent Res 2000; 14:5-102.
7. Kaufman E, Lamster I B: Analysis of saliva for periodontal diagnosis—a review, J Clin Periodontol 2000; 27:453-65.
8. Streckfus C F, Bigler L R: Saliva as a diagnostic fluid, Oral Dis 2002; 8:69-76.
9. Rossomando E F, Kousvelari E, Janicki B W, Tabak L A: Improvement of oral health in the postgenomic era: opportunities for government/industry partnerships, Compend Contin Educ Dent 2001; 22:570-2, 574.
10. Tabak L A: A revolution in biomedical assessment: the development of salivary diagnostics, J Dent Educ 2001; 65:1335-9.
11. Cordeiro M L, Turpin C S, McAdams S A: A comparative study of saliva and OraSure oral fluid, Ann NY Acad Sci 1993; 694:330-1.
12. Rehak N N, Cecco S A, Csako G: Biochemical composition and electrolyte balance of "unstimulated" whole human saliva, Clin Chem Lab Med 2000; 38:335-43.
13. Soderling E: Practical Aspects of Salivary Analysis, Human Saliva: Clinical Chemistry and Microbiology, 1-24. Vol. 1, Boca Raton, CRC Press, 1989.
14. Seymour E: Salivary sampling device and sample adequacy system: U.S. Pat. No. 5,393,496. Patent and Trademark Office, United States, Salivary Diagnostic Systems, Vancouver, Wash., 1995.
15. Goldstein A S, Gadojdea S, Zogg D F: Oral collection device and method for immunoassay: U.S. Pat. No. 5,335,673. Patent and Trademark Office, United States, Epitope, Inc., Beaverton, Oreg., 1994.
16. McKie A, Vyse A, Maple C: Novel methods for the detection of microbial antibodies in oral fluid, Lancet Infect Dis 2002; 2:18-24.
17. Marcus E R, Jooste C P, Driver H S, Hattingh J: The quantification of individual proteins in crevicular gingival fluid, J Periodontal Res 1985; 20:444-9.
18. Burke J C, Evans C A, Crosby T R, Mednieks M I: Expression of secretory proteins in oral fluid after orthodontic tooth movement, Am J Orthod Dentofacial Orthop 2002; 121:310-5.
19. Slots Jr, Taubman M A: Contemporary oral microbiology and immunology, 649, St. Louis, Mosby-Year Book, 1991.
20. Thieme T R, Goldstein A S, Piacentini S C, Klimkow N M: Oral Collection Device and Kit: U.S. Pat. No. 5,830,410. Patent and Trademark Office, United States, Epitope, Inc., Beaverton, Oreg., 1998.
21. Cimasoni G: The crevicular fluid, Monographs in oral science; Vol. 3, 122, Basel, New York, S. Karger, 1974.
22. Lehner T: The Borderland between caries and periodontal disease : Proceedings of a conference sponsored by the Royal Society of Medicine, 28 Feb. 1977, London, New York, 1977. Academic Press, Grune & Stratton.
23. Steenhuysen J: Orasure, Abbott agree to co-distribute HIV test. Reuters, Chicago, 2002.
24. Roitt I M, Lehner T: Immunology of Oral Diseases, pp. 464, Oxford, Blackwell Scientific Publications, 1981.
25. Gallo D, George J R, Fitchen J H, Goldstein A S, Hindahl M S: Evaluation of a system using oral mucosal transudate for HIV-1 antibody screening and confirmatory testing. OraSure HIV Clinical Trials Group, JAMA 1997; 277:254-8.
26. Thieme T, Piacentini S, Davidson S, Steingart K: Determination of measles, mumps, and rubella immunization status using oral fluid samples, JAMA 1994; 272:219-21.
27. Bull A R, Kimmance K J, Parry J V, Perry K R: Investigation of an outbreak of hepatitis A simplified by salivary antibody testing, Epidemiol Infect 1989; 103:371-6.
28. Parry J V, Perry K R, Panday S, Mortimer P P: Diagnosis of hepatitis A and B by testing saliva, Journal Med Virol Aug 1989; 28:255-60.
29. Sherman K E, Creager R L, O'Brien J, Sargent S, Piacentini S, Thieme T: The use of oral fluid for hepatitis C antibody screening, Am J Gastroenterol 1994; 89:2025-7.
30. Patel P, Mendall M, Khulusi S, et al.: Salivary antibodies to *Helicobacter pylori*: screening dyspeptic patients before endoscopy, Lancet 1994; 344:511-4.
31. Parry J V, Perry K R, Mortimer P P: Sensitive assays for viral antibodies in saliva: an alternative to tests on serum, Lancet 1987; 2:72-5.
32. Barros M, Duarte Neto A N, Pereira V R, et al.: Evaluation of oral mucosal transudate for immunodiagnosis of Chagas' disease, Rev Inst Med Trop Sao Paulo 1999; 41:265-6.
33. Tencza, S., Islam, K., Kalia, V., Nasir, M., Jolley, M., Montelaro, R. 2000. Development of a fluorescence polarization-based diagnostic assay for equine infectious anemia virus. J. Clin Microbiol. 38: 1854-9.
34. Lin, M., Sugden, E., Jolley, M., Stilwell, K. 1996. Modification of the *Mycobacterium bovis* extracellular protein MPB70 with fluorescein by fluorescence polarization. Clin Diag. Lab Immunol. 3: 438-43.
35. Nielsen K, Gall D, Jolley M, et al.. 1996. A homogeneous fluorescence polarization assay for detection of antibody to *Brucella abortus*, J Inmunolog Methods 195:161-8.
36. Adams, C, Boge, A. Gaudet L. 2003. HTS Platform for Determining Enzyme Activity Assay Tutorial. Genetic Engineering News 23(20) 38-39.
37. Gallo, D., George, J. R., Fitchen, J. H., Goldstein, A. S., Hindahl, M. S., 1997. Evaluation of a system using oral mucosal transudate for HIV-1 antibody screening and confirmatory testing. OraSure HIV Clinical Trials Group, JAMA 277: 254-8.
38. Thieme, T., Piacentini, S., Davidson, S., Steingart, K. 1994. Determination of measles, mumps and rubella immunization status using oral fluid samples. JAMA 272: 219-21.

39. Bull, A. R., Kimmance, K. J., Parry, J. V., Perry, K. R. 1989. Investigation of an outbreak of hepatitis A simplified by salivary antibody testing. Epidemiol. Infect. 103: 371-6.
40. Parry, J. V., Perry, K. R., Panday, S., Mortimer, P. P. 1989. Diagnosis of hepatitis A and B by testing saliva. Journal Med. Virol. 28 (Aug): 255-60.
41. Sherman, K. E., Creager, R. L., O'Brien, J., Sargent, S., Piacentini, S., Thierme, T. 1994. The use of oral fluid for hepatitis C antibody screening. Am J. Gastrogenterol. 89: 2025-7.
42. Patel, P., Mendall, M., Khulusi, S., Molineaux, N., Levy, J., Maxwell, J. D., Northfield, T. S. 1994. Salivary antibodies to *Helicobacter pylori*: screening dyspeptic patients before endoscopy. Lancet 344: 511-514.
43. Parry, J. V., Perry, K. R., Mortimer, P. P. 1987. Sensitive assays for viral antibodies in saliva: an alternative t tests on serum. Lancet 2: 72-5.
44. Rossomando, E. F., Kousvelari, E., Janicki, B. W., Tabak, L. A. 2001. Improvement of oral health in th postgenomic era: opportunities for government/industry partnerships, Compend. Contin. Educ. Dent. 22: 570-4.
45. Tabak, L. A. 2001. A revolution in biomedical assessment: the development of salivary diagnostics. J. Dent Educ. 65: 1335-9.
46. Gunderson, E. K., Garland, C., Hourani, L. L. 1995. Infectious disease rates in the U.S. Navy, 1980 to 1995. Mil. Med. 166: 544-9.
47. Behr, M. A. 2004. *Tuberculosis* due to multiple strains: a concern for the patient? A concern for *tuberculosis* control? Am. J. Respir. Crit. Care. Med. 169 (5): 554-5.
48. Sellman, B., Mourez, M., Collier, R. 2001. Dominant-negative mutants of a toxin subunit: An approach to therapy of anthrax. Science 292: 695-7.
49. Petosa, D., Collier, R., Klimpel, K., Leppla, S., Liddington, R. 1997. Crystal structure of the anthrax toxin protective antigen. Nature 385: 833-8.
50. Little, S. F., Novak, J., Lowe, J., Singh, Y., Klimpel, K. R., Lingerding, B. C., and Friedlander, A. M. 1996. Characterization of lethal factor binding and cell receptor binding domains of protective antigen of *Bacillus anthracis* protective antigen. Microbiology 142: 707-15.
51. Brossier, F., Sirard, J-C., Guidi-Rontani, C., Duflot, E., Mock., M. 1999. Functional analysis of the carboxy-terminal domain of *Bacillus anthracis* protective antigen. Infect. Immun. 67: 964-7.
52. Brossier, F., Weber-Levy, M., Mock, M., Sirard, J. 2000. Role of toxin functional domains in anthrax pathogenesis. Infect. Immun. 68: 1781-6.
53. Mogridge, J., Moourez, M., Collier, R. 2001. Involvement of domain 3 in oligomerization by the protective antigen moiety of anthrax toxin. J. Bacteriol. 183: 2111-6.
54. Brachman, P., Gold, H., Plotkin, S., Fekety, F., Werrin, M., Ingraham, N. 1962. Field evaluation of a human anthrax vaccine. Am. J. Public Health 52: 632-45.
55. Fellows, P., Linscott, M., Ivins, B., Pitt, M. L. M., Rossi, C. A., Gibbs, P. H., and Friedlander, A. M. 2001. Efficacy of a human anthrax vaccine in guinea pigs, rabbits, and rhesus macaques against challenge by *Bacillus anthracis* isolates of diverse geographical origin. Vaccine 19: 3241-7.
56. Turnbull, P., Broster, M., Carman, J., Manchee, R., Melling, J. 1986. Development of antibodies to protective antigen and lethal factor components of anthrax toxin in humans and guinea pigs and their relevance to protective immunity. Infect Immun. 52: 356-63.
57. Kowski T, Wu J: Fluorescence polarization is a useful technology for reagent reduction in assay miniaturization, Comb Chem High Throughput Screen 2000; 3:437-44.
58. ONR: Future Naval Capabilities: Warfighter Protection, Washington, D.C., Department of the Navy: Science and Technology Lead, 1992.
59. Terpetschnig E, Szmacinski H, Lakowicz J: Fluorescence polarization immunoassay of a high-molecular-weight antigen based on a long-lifetime Ru-ligand complex, Anal Biochem 1995; 227:140-7.
60. Tencza S, Islam K, Kalia V, Nasir M, Jolley M, Montelaro R: Development of a fluorescence polarization-based diagnostic assay for equine infectious anemia virus, J Clin Microbiol 2000; 38:1854-9.
61. Schade S, Jolley M: Fluorescence polarization assays of enzymes and substrates thereof: U.S. Pat. No. 5,804, 395. Patent and Trademark Office, United States, Secretary of the Navy, 1998.
62. Nasir M, Jolley M: Fluorescence polarization: An analytical tool for immunoassay and drug discovery, Comb Chem High Throughput Screen 1999; 2:177-90.
63. Nasir M, Jolley M: Fluorescence polarization: Stretching it to its limits. A special edition on fluorescence polarization., Comb Chem High Throughput Screen 2002; in press.
64. Jolley M: Fluorescence polarization immunoassay for the determination of therapeutic drug levels in human plasma, J Anal Toxicology 1981; 5:236-40.
65. Lin M, Sugden E, Jolley M, Stilwell K: Modification of the *Mycobacterium bovis* extracellular protein MPB70 with fluorescein by fluorescence polarization, Clin Diag Lab Immunol 1996; 3:438-43.
66. Nielsen K, Gall D, Jolley M, et al.: A homogeneous fluorescence polarization assay for detection of antibody to *Brucella abortus*, J Immunolog Methods 1996; 195: 161-8.
67. Cui, H. H., Valdez, J. G., Steinkamp, J. A., Crissman, H. A. 2003. Fluorescence lifetime-based discrimination and quantification of cellular DNA and RNA with phase-sensitive flow cytometry. Cytometry 52A(1): 46-55.
68. Morrison, L. E. 1988. Time-resolved detection of energy transfer: theory and application to immunoassays. 174(1): 101-20.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. A competitive method for detecting *Bacillus anthracis* in a sample comprising the steps:
   a. intermixing said sample, with a specific antibody to *Bacillus anthracis* protective antigen, and a competitive reagent comprising a *Bacillus anthracis* polypeptide labeled with a fluorochrome capable of binding to said specific antibody, to produce a mixture;
   b. incubating said mixture for 15 seconds to 5 minutes;
   c. measuring the fluorescence polarization of said mixture, a negative control solution of said fluorochrome-labeled competitive reagent, and a positive control solution of said fluorochrome-labeled competitive reagent exposed to a known amount of said *Bacillus anthracis* protective antigen;

d. detecting binding interaction between said *Bacillus anthracis* protective antigen in the sample and said antibody by comparing the measured fluorescence polarization of said mixture with the measured fluorescence polarization of said negative control solution, and said positive control solution.

2. The method of claim 1, wherein said competitive reagent is native or recombinant *Bacillus anthracis* polypeptides.

3. The method of claim 1, wherein said protein can be detected down to less than 5 μ/ml or 6 nM within 5 minutes.

4. The method of claim 1 wherein said sample is selected from the group consisting of broth culture media of growing *Bacillus anthracis* or bodily fluids.

5. The method of claim 1, wherein said incubation step (b) occurs in less than 30 seconds for samples suspected of containing high concentration of said *Bacillus anthracis* protective antigen.

6. The method of claim 1 wherein said incubation step (b) occurs in 4 to 5 minutes for samples suspected of containing low concentration of said *Bacillus anthracis* protective antigen.

7. The method of claim 1 wherein said fluorochrome is pH independent.

8. The method of claim 1 wherein said fluorochrome is selected from the group consisting of 7-AAD, Acridine Orange, Alexa 488, Alexa 532, Alexa 546, Alexa 568, Alexa 594, Aminonapthalene, Benzoxadiazole, BODIPY 493/504, BODIPY 505/515, BODIPY 576/589, BODIPY FL, BODIPY TMR, BODIPY TR, Carboxytetramethylrhodamine, Cascade Blue, a Coumarin, Cy2, CY3, CY5, CY9, Dansyl Chloride, DAPI, Eosin, Erythrosin, Ethidium Homodimer II, Ethidium Bromide, Fluorescamine, Fluorescein, FTC, GFP (yellow shifted mutants T203Y, T203F, S65G/S72A), Hoechst 33242, Hoechst 33258, IAEDANS, an Indopyras Dye, a Lanthanide Chelate, a Lanthanide Cryptate, Lissamine Rhodamine, Lucifer Yellow, Maleimide, MANT, MQAE, NBD, Oregon Green 488, Oregon Green 514, Oregon Green 500, Phycoerythrin, a Porphyrin, Propidium Iodide, Pyrene, Pyrene Butyrate, Pyrene Maleimide, Pyridyloxazole, Rhodamine 123, Rhodamine 6G, Rhodamine Green, SPQ, Texas Red, TMRM, TOTO-1, TRITC, YOYO-1, vitamin B12, flavin-adenine dinucleotide, and nicotinamide-adenine dinucleotide.

9. The method of claim 1 wherein said fluorochrome concentration is 1 nM or less and the measured fluorescence polarization of said mixture is increased or decreased by at least 10 mP.

10. The method of claim 1 wherein the said antibody is polyclonal or monoclonal.

11. The method of claim 4, wherein said bodily fluids are selected from the group consisting of saliva, oral rinse expectorant, oral fluid including oral mucosal transudate and gingival crevicular fluid, urine, sweat, tears, blood, serum, stool, gastric fluid, synovial fluid, and phlegm.

* * * * *